(12) United States Patent
Bateman et al.

(10) Patent No.: US 8,783,254 B2
(45) Date of Patent: Jul. 22, 2014

(54) TRACHEOSTOMY TUBES

(75) Inventors: Timothy Bateman, Dymchurch (GB); Stephen James Field, Canterbury (GB)

(73) Assignee: Smiths Group PLC, London (GB)

( * ) Notice: Subject to any disclaimer, the term of this patent is extended or adjusted under 35 U.S.C. 154(b) by 1197 days.

(21) Appl. No.: 11/886,586

(22) PCT Filed: Mar. 6, 2006

(86) PCT No.: PCT/GB2006/000767
§ 371 (c)(1),
(2), (4) Date: Sep. 18, 2007

(87) PCT Pub. No.: WO2006/100424
PCT Pub. Date: Sep. 28, 2006

(65) Prior Publication Data
US 2009/0050157 A1    Feb. 26, 2009

(30) Foreign Application Priority Data

Mar. 19, 2005  (GB) .................................. 0505724.5

(51) Int. Cl.
*A61M 16/04*  (2006.01)

(52) U.S. Cl.
USPC .................................. 128/207.14; 128/200.26

(58) Field of Classification Search
CPC .......................... A61M 16/04–16/0472; A61M 2016/04–2016/0431
USPC ............. 128/200.24, 200.26, 207.14–207.17, 128/207.29
See application file for complete search history.

(56) References Cited

U.S. PATENT DOCUMENTS

| | | | | |
|---|---|---|---|---|
| 3,682,166 A * | 8/1972 | Jacobs | ..................... | 128/205.19 |
| 3,884,242 A * | 5/1975 | Bazell et al. | ............. | 128/207.15 |
| 4,269,184 A * | 5/1981 | Montgomery | ........... | 128/207.14 |
| 4,471,776 A * | 9/1984 | Cox | ......................... | 128/207.15 |
| 4,498,473 A * | 2/1985 | Gereg | ...................... | 128/207.15 |
| 4,612,927 A * | 9/1986 | Kruger | ..................... | 128/200.26 |
| 4,722,335 A * | 2/1988 | Vilasi | ....................... | 128/207.14 |
| 4,987,895 A * | 1/1991 | Heimlich | ................. | 128/207.14 |
| 4,990,143 A * | 2/1991 | Sheridan | ....................... | 604/526 |
| 5,297,546 A * | 3/1994 | Spofford et al. | ......... | 128/207.14 |
| 5,353,787 A * | 10/1994 | Price | ........................ | 128/200.26 |
| 5,609,629 A * | 3/1997 | Fearnot et al. | ............... | 623/1.42 |
| 5,695,482 A * | 12/1997 | Kaldany | ....................... | 604/526 |
| 6,135,111 A * | 10/2000 | Mongeon | ................. | 128/207.15 |
| 6,148,818 A * | 11/2000 | Pagan | ...................... | 128/207.15 |
| 6,382,207 B1 * | 5/2002 | Giuffre et al. | ............. | 128/202.24 |
| 6,536,437 B1 * | 3/2003 | Dragisic | .................. | 128/207.18 |
| 7,100,612 B2 * | 9/2006 | Dunlap | .................... | 128/207.18 |
| 7,291,240 B2 * | 11/2007 | Smith et al. | .................... | 156/195 |
| 7,918,819 B2 * | 4/2011 | Karmarkar et al. | ........ | 604/95.01 |
| 2003/0172933 A1 * | 9/2003 | Nimmo | ..................... | 128/207.14 |
| 2004/0116551 A1 * | 6/2004 | Terry | ............................. | 523/122 |
| 2006/0074372 A1 * | 4/2006 | Haga et al. | ..................... | 604/19 |

FOREIGN PATENT DOCUMENTS

| | | |
|---|---|---|
| EP | 1092448 | 4/2001 |
| WO | 01/78825 | 10/2001 |
| WO | 2004/050160 | 6/2004 |

* cited by examiner

*Primary Examiner* — Justine Yu
*Assistant Examiner* — LaToya M Louis
(74) *Attorney, Agent, or Firm* — Louis Woo

(57) ABSTRACT

A tracheostomy tube has an inner skeletal frame (40) of a relatively stiff plastics material having a longitudinal spine (45) and several annular ribs (42) extending around the frame. A thin, flexible plastics sheath (41) is bonded to the outside of the frame (40). The construction enables a maximum internal diameter with a minimum external diameter.

13 Claims, 2 Drawing Sheets

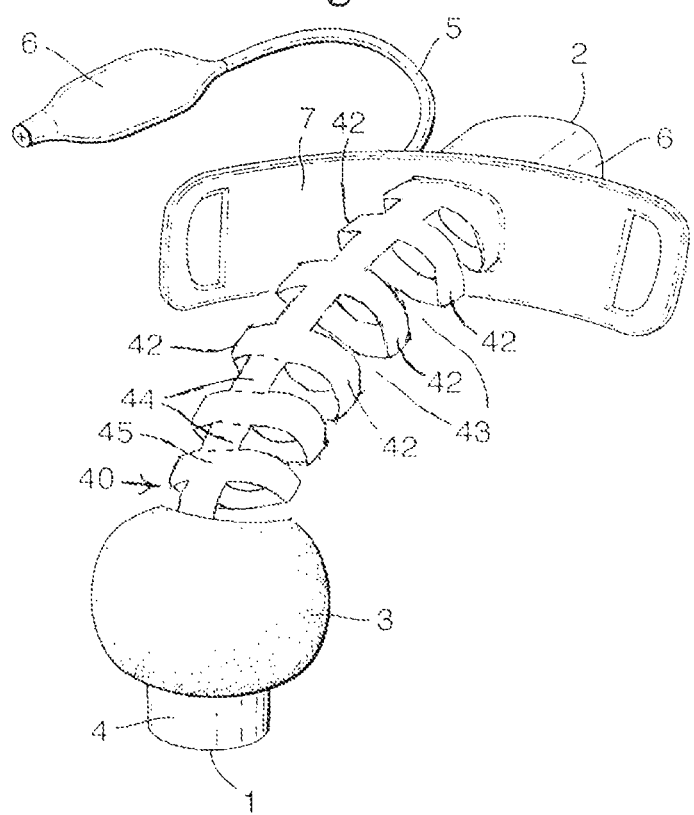

TRACHEOSTOMY TUBES

FIELD OF INVENTION

This invention relates to tracheostomy tubes.

BACKGROUND OF INVENTION

Tracheostomy tubes are used to provide a passage for ventilation gas to the trachea of a patient through a surgically-made opening in the throat. The tubes may be of various different kinds. The tube may simply comprise an extruded or moulded hollow plastics shaft shaped appropriately for the patient's anatomy. Alternatively, the tube may be reinforced by means of a helical metal wire or a stiff, helical plastic element. A tube reinforced in this way is protected against radial crushing forces and helps prevent kinking. This enables a softer, more flexible plastics to be used, which enables the tube itself to be relatively flexible.

When performing a tracheostomy, the opening made should be as small as possible, in order to minimize trauma to the patient. This suggests that a tube with a small external diameter is preferable. The problem with using a smaller diameter tube, however, is that this restricts the size of the bore through the tube, making ventilation less efficient and making breathing by the patient more difficult. The problem, therefore, is to achieve a tube with a thin wall so that the bore can be as large as possible and the external diameter can be as small as possible, whilst still maintaining sufficient strength in the tube to resist crushing.

It is an object of the present invention to provide an alternative tracheostomy tube.

BRIEF SUMMARY OF INVENTION

According to the present invention there is provided a tracheostomy tube, characterised in that the tube has a skeletal structural member of a relatively stiff plastics material and of generally tubular form, that the structural member has a plurality of rib members spaced along the length of the member, the rib members extending circumferentially of the structural member and linked with one another by longitudinal members, and that the tube has a flexible sheath of a plastics material attached with the structural member.

Preferably the sheath is attached with the outside of the structural member and is thinner than the structural member. Preferably the longitudinal members are aligned with one another to provide a longitudinal spine of the structural member. The tube may be curved along its length and the spine may extend along the outside curve of the tube. The structural member may have a conduit extending along the length of the spine. Each rib member preferably extends in a complete circle around the structural member. The structural member may be of polycarbonate and the sheath may be of PVC.

BRIEF DESCRIPTION OF DRAWINGS

A tracheostomy tube according to the present invention, will now be described, by way of example, with reference to the accompanying drawing, in which:

FIG. 1B is a perspective view of the tube showing the skeletal frame without the sheath covering the frame.

DETAILED DESCRIPTION OF INVENTION

Figure 1A:
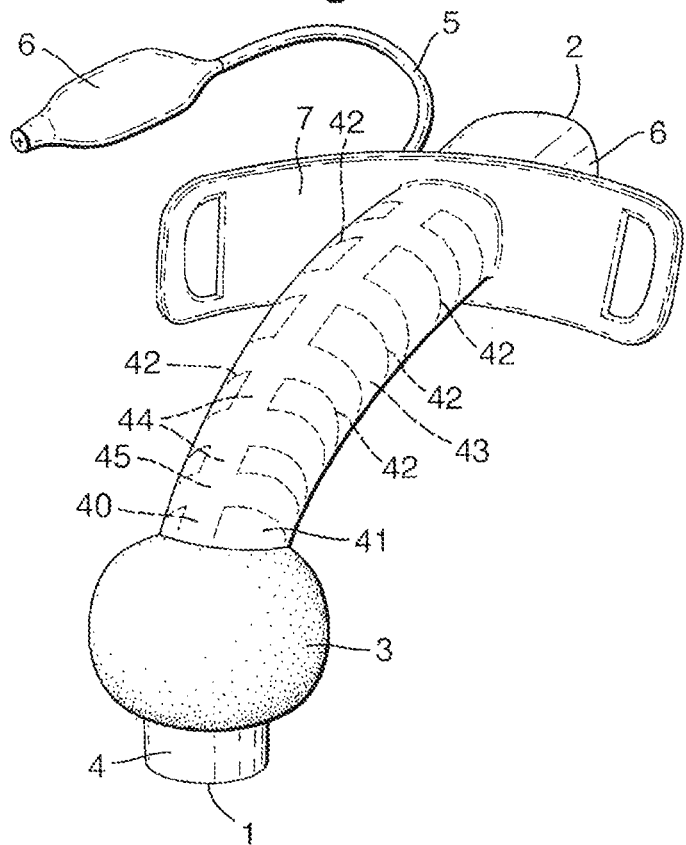
FIG. 1A is a perspective view of the tube.

The tube is curved along its length, to conform to the anatomy of the patient, from its forward, patient end 1 to its rear, machine end 2. Alternatively, the tube could be straight and sufficiently flexible to conform to the shape of the anatomy. Towards its patient end 1 the tube has a large-volume, low-pressure sealing cuff 3 embracing the outside of a shaft 4. The cuff 3 is inflatable and deflatable, in the usual way, by means of an inflation line 5 having a balloon and connector 8 at its machine end. At its rear end 2, the tube has a standard 15 mm connector 6 and a neck flange 7.

As so far described, the tube is conventional. Where the tube differs from previous tubes is that the tube shaft 4 is made of two separate components, namely a skeletal, structural member or frame 40 and a sheath 41 attached to the outside of, and covering, the frame. The outside of the sheath 41, in use, contacts tissue of the tracheostomy.

Figure 2:
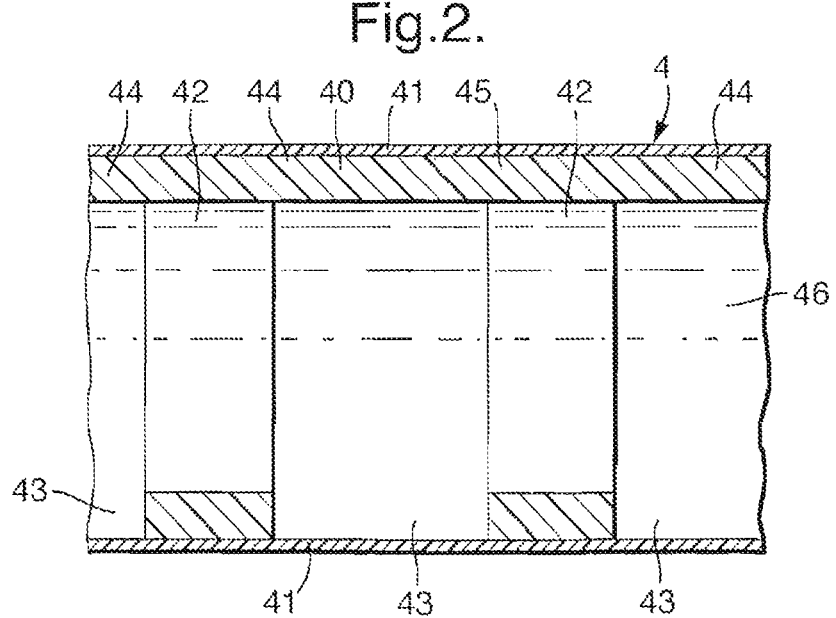
FIG. 2 is an enlarged cross-sectional side elevation view along a part of the length of the tube.

The frame 40 is an integral, one-piece moulding of a relatively stiff plastics material, such as polycarbonate. The frame 40 comprises nine annular ribs or rings 42, only six of which are shown in the drawing, which extend circumferentially around the tube as complete circles, per shown for example in FIG. 1B. Alternatively, the ribs need not be complete circles and could be present in different numbers. The ribs 42 are spaced equally from one another along the length of the shaft 4 and are separated from one another by gaps 43. As shown in FIG. 1B, the ribs 42 are supported relative to one another by longitudinal members 44, which in the present example are arranged in a line to form a single spine 45 extending in axial alignment along the outside of the curve of the shaft 4. Two of the longitudinal members 44 are identified in FIG. 1B to be between respective sets of dotted lines along spine 45. That spine 42 is continuous is moreover shown in cross section in FIG. 2 where reference number 45 designates the continuous spine. The spine 45 could include a conduit extending along its length to provide an air passage (not shown) between the inflation line 5 and the interior of the cuff 3. In other examples, the longitudinal members need not be aligned with one another but could, for example, be staggered around the shaft. The continuous nature of the spine 45, in the present arrangement, gives the shaft 40 a relatively high strength to resist axial compression forces, which can be met during insertion through neck tissue. It also helps define the curve and plane of curvature of the shaft 4. The frame 40 has a wall thickness of around 0.75 mm, which is the same for the ribs and the longitudinal members, although the thickness of the ribs and longitudinal members could be different. The width of the ribs and longitudinal members is greater than their thickness, typically being about 5 mm.

The sheath 41 is in the form of a thin film of a flexible plastics material, such as plasticised PVC and has a wall thickness of 0.3 mm, making it substantially thinner than the frame 40. The sheath 41 may be assembled on the frame 40 by overmoulding or dipping. It will be appreciated that the materials used for the frame 40 and the sheath 41 should be compatible so that the sheath bonds securely to the frame. The thickness of the shaft 4 in the region of the film 41 is considerably less than in conventional tracheostomy tubes, which have a wall thickness around 2 mm. Even the frame 40 itself is thinner than the wall of conventional tubes, which is possible because the material from which it is made is relatively hard compared with conventional tubes. In some arrangements the sheath could have the same thickness as the frame and the sheath may be moulded about the frame so that the frame is incorporated into the thickness of the wall of the sheath.

The tube is inserted through a surgically made opening into the trachea in the usual way with the external surface of the sheath 41 contacting the neck tissue through the opening and with the internal surface of the sheath and the frame 40 providing a bore 46 for passage of ventilation gas into and out of the trachea. The frame 40 gives the tube sufficient axial rigidity and the desired degree of flexibility. The frame 40 enables a very low wall thickness compared with conventional tubes yet with the necessary mechanical properties. The thin wall enables the diameter of the bore 46 through the tube to be maximised for a minimum external diameter, thereby minimizing trauma to the patient. The small thickness of the sheath 41 may result in a slightly ribbed external surface feel to the shaft but this is not believed to make insertion significantly more difficult.

The invention claimed is:

1. A tracheostomy tube, characterized in that the tube has a one-piece skeletal structural frame of a relatively stiff plastics material and of generally tubular form, that the structural frame comprises a longitudinal spine formed from longitudinal members and a plurality of rib members extending circumferentially from respective longitudinal members so as to be spaced along the length of the structural frame, the rib members extending circumferentially of the structural frame and linked with one another by the longitudinal members, and that the tube has a flexible sheath of a plastics material attached with the structural frame, wherein the sheath is thinner than the structural frame.

2. A tracheostomy tube according to claim 1, characterized in that the sheath is attached with the outside of the structural frame.

3. A tracheostomy tube according to claim 1, characterized in that the longitudinal members are aligned with one another to provide the longitudinal spine of the structural frame.

4. A tracheostomy tube according to claim 3, characterized in that the tube is curved along its length and the spine extends along the outside curve of the tube.

5. A tracheostomy tube according to claim 3, characterized in that the structural frame has a conduit extending along the length of the spine.

6. A tracheostomy tube according to claim 1, characterized in that each rib member extends in a complete circle around the structural frame.

7. A tracheostomy tube according to claim 1, characterized in that the structural frame is of polycarbonate.

8. A tracheostomy tube according to claim 1, characterized in that the sheath is of PVC.

9. A tracheostomy tube, characterized in that the tube is of generally tubular form and comprises an integral one piece skeletal structure of a relatively stiff plastics material in the shape of a longitudinal spine with a plurality of rib members extending from said spine and spaced along the length of said spine, the spine extending in axial alignment along the outside curve of said tube and the rib members extending transversely from the spine in a circumferential manner to form respective annular rings, and that the tube has a flexible sheath of a plastics material attached with the skeletal structure, wherein the sheath is thinner than the skeletal structure.

10. A tracheostomy tube according to claim 9, characterized in that each rib member extends from said spine in a complete circle.

11. A tracheostomy tube comprising a skeletal structural frame and a sheath covering said frame, said frame having a plurality of ribs separated from each other by gaps each extending circumferentially around the tube, said ribs being spaced from one another along the length of the tube and are supported relative to one another by longitudinal members that are arranged in a line to form a spine extending in axial alignment along the tube, said sheath being a film of plastics material and said frame being made from a relatively stiff plastics material, wherein the sheath is thinner than the frame.

12. A tracheostomy tube according to claim 11, wherein the longitudinal members are in alignment with each other so that the spine is formed as a single continuous spine.

13. A tracheostomy tube according to claim 11, wherein the longitudinal members are not in alignment with each other but are staggered around the tube.

* * * * *